(12) United States Patent
Karason et al.

(10) Patent No.: US 7,094,212 B2
(45) Date of Patent: Aug. 22, 2006

(54) RIGID DRESSING

(75) Inventors: Gudjon G. Karason, Sollentuna (SE); Anton Johannesson, Sibbhult (SE)

(73) Assignee: Ossur hf, Reykjavik (IS)

( * ) Notice: Subject to any disclaimer, the term of this patent is extended or adjusted under 35 U.S.C. 154(b) by 124 days.

(21) Appl. No.: 10/681,134

(22) Filed: Oct. 9, 2003

(65) Prior Publication Data

US 2004/0073152 A1  Apr. 15, 2004

Related U.S. Application Data

(60) Provisional application No. 60/417,556, filed on Oct. 11, 2002.

(51) Int. Cl.
*A61F 5/00* (2006.01)
*A61F 13/00* (2006.01)
*A61F 15/00* (2006.01)

(52) U.S. Cl. ............................ 602/5; 602/13; 602/42

(58) Field of Classification Search ............ 602/41–43, 602/48, 13, 2; 607/96, 108–112
See application file for complete search history.

(56) References Cited

U.S. PATENT DOCUMENTS

| 3,186,405 | A |   | 6/1965 | Bailey et al. |
| 3,212,497 | A |   | 10/1965 | Dickinson |
| 4,157,713 | A |   | 6/1979 | Clarey |
| 5,190,033 | A | * | 3/1993 | Johnson ....................... 607/108 |
| 5,431,622 | A | * | 7/1995 | Pyrozyk et al. ................. 602/2 |

\* cited by examiner

*Primary Examiner*—Henry Bennett
*Assistant Examiner*—Kari Petrik
(74) *Attorney, Agent, or Firm*—Bacon & Thomas

(57) ABSTRACT

A wound dressing for a body member including a sealed casing formed of a flexible, air impermeable material configured and dimensioned to accommodate and enclose a body member, a compactible filler material disposed in the interior of the casing, and a valve communicating with the interior of the casing for evacuating air therefrom, whereupon the filler material interengages to combine with the casing to form a rigid structure conforming to a body member.

8 Claims, 3 Drawing Sheets

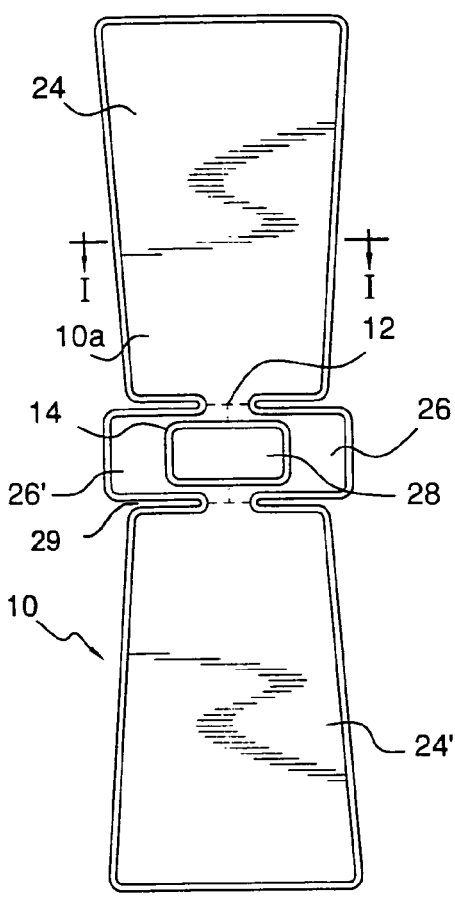
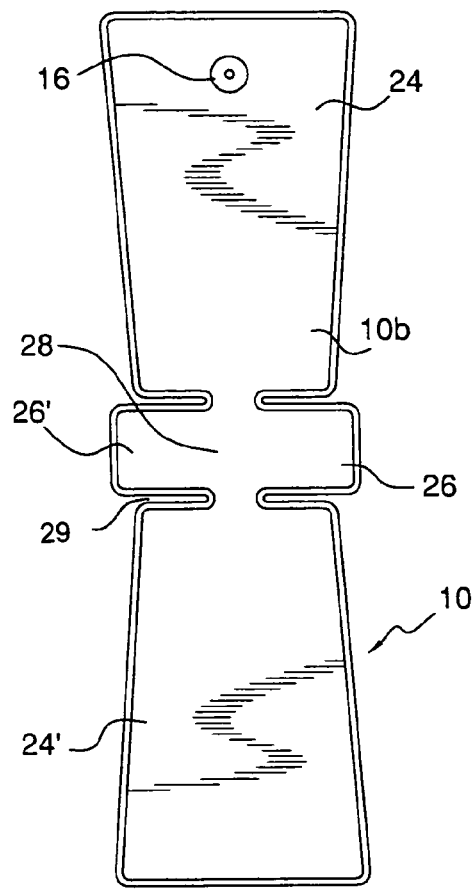
FIG.1  FIG.2
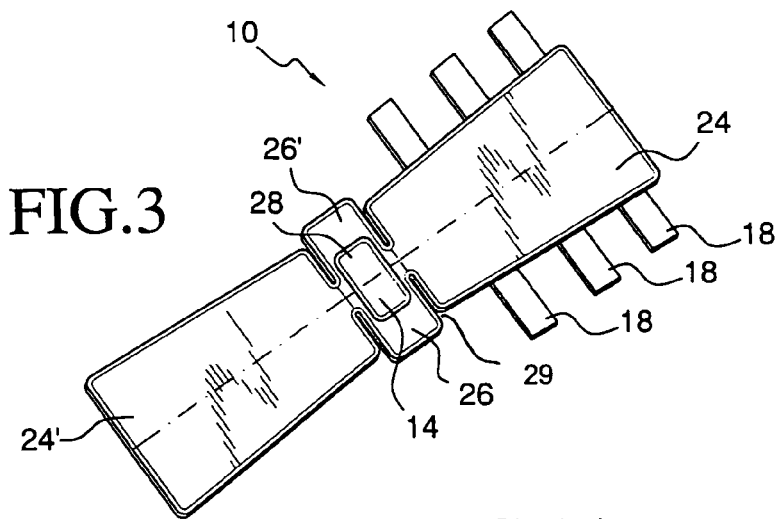
FIG.3
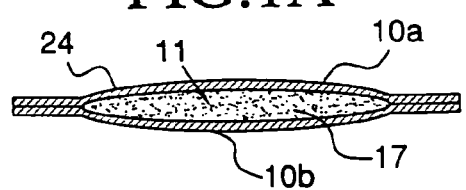
FIG.1A

RIGID DRESSING

This application claims the benefit of Provisional Patent Application Ser. No. 60/417,556, filed Oct. 11, 2002.

BACKGROUND OF THE INVENTION

1. Field of the Invention

The present invention pertains to a wound dressing, and more particularly to a rigid dressing for a residual limb immediately after surgical amputation of a limb.

2. Background of the Invention

Postoperative treatment of a residual limb after surgical amputation is conducted to ensure primary wound healing and pain control, reduce edema and assist in proper residual limb formation. Conventional postoperative treatment involves soft dressings of sterile gauze and padding followed by a compressive bandage of elastic wrap. These dressings suffer from the disadvantages in that the elastic wrap can generate high pressure on the residual limb and the dressing is cumbersome to remove when inspection of the wound is required.

An alternative technique is to provide a rigid dressing wherein a nonremovable rigid plaster dressing is applied to the residual limb immediately after limb removal. Although the plaster dressing immobilizes the residual limb, it suffers from several significant disadvantages. Significant disadvantages to this postoperative dressing include the fact that it requires substantial time and skill to apply the plaster dressing. Another disadvantage is that inspection of the residual limb cannot be conducted without breaking and removing the plaster casting from the limb.

The present invention overcomes the disadvantages of the prior art by providing a rigid wound dressing which is easily configured to enclose a residual limb immediately after surgical amputation while firmly securing the residual limb and permitting easy inspection of the residual limb without destruction of the dressing.

SUMMARY OF THE INVENTION

According to one embodiment of the present invention, there is provided a sealed casing containing an compactable filler material disposed in the interior thereof, with the casing formed of a flexible, air impermeable material that is configured and dimensioned to accommodate a body member. The invention includes an appropriate arrangement permitting communication with the interior of the casing for evacuating air therefrom, whereupon the filler material interengages, in the aggregate, to form a rigid structure conforming to the body member. The sealed casing is divided into portions which are connected to one another but which can be flexed at predetermined points or areas relative to a central portion of the wound dressing after interengagement of the filler material. A pad is connected to the central portion to accommodate a distal end of a body member.

Significant aspects and features of the present invention include a wound dressing capable of being formed into a rigid structure which enables for ease of application to and inspection of the body member. Particularly, the flexible nature and inherent shape of the casing permit portions of the rigid dressing to be flexed and therefore removed from the body member for inspection of the body member without destruction of the dressing.

Another significant aspect and feature of the present invention is a wound dressing which provides for rigid securement of a body member which is easily and quickly performed while providing comfort and safety to the body member.

Although described in the context of securing a residual limb immediately after surgical amputation of a limb, the present invention is not intended to be limited to the securement of residual limbs. Instead, the present invention is directed to any application where securement and inspection of a body member is necessitated in a simple and quick fashion.

BRIEF DESCRIPTION OF THE DRAWINGS

FIG. 1 is a plan view of the sealed casing of the present invention.

FIG. 1A is a cross-sectional view taken along line I—I in FIG. 1.

FIG. 2 is a plan view showing the interior of the sealed casing.

FIG. 3 is a perspective view showing the sealed casing.

DETAILED DESCRIPTION OF THE INVENTION

Figure 4:
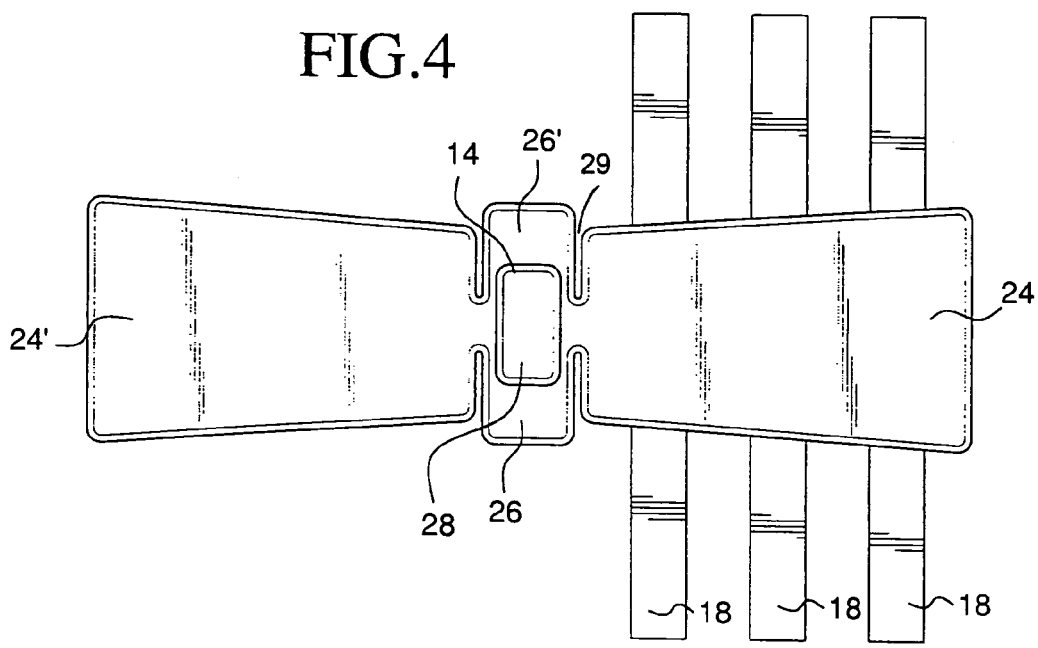
FIG. 4 is a perspective view showing the wound dressing in an extended configuration.

FIG. 1 illustrates a plan view of a sealed casing 10 made of a flexible, air impermeable sheet material such as a polymer coated textile or polymer film and defining an interior volume 11. The casing 10 may be formed of two adjoining sheets 10a and 10b, for example, as shown in FIG. 1a, and is divided into opposing elongated flaps or longitudinal portions 24, 24', opposing lateral flaps or central lateral portions 26, 26' and a central portion 28 positioned between the longitudinal portions 24, 24' and lateral portions 26, 26'. At least one recess 29 may be defined between the longitudinal portions 24, 24' and the adjoining central portion 28. A valve 16 is positioned along one of the longitudinal portions 24, 24' and arranged to communicate with the interior of the casing. Any device or arrangement suitable for providing sealable access to the interior of the casing could be used in place of the valve 16.

Disposed in the interior of the casing 10 is a filler material 17 that interengages, in the aggregate, to form the casing 10 into a rigid structure conforming to a body member when air is evacuated from the sealed casing 10 via the valve 16. The filler material 17 (FIG. 1a) includes particles within a predetermined size range which is compressible or incompressible when compacted. The particles may include beads, grains, powder or organic material that can be arranged to interengage upon evacuation of air from the sealed vacuum. Specific types of filler material 17 may include thermoplastic and thermoset materials, both foam and solid, and sand.

FIG. 2 illustrates the interior of the casing 10 without the filler material 17 and shows the division 12 of the longitudinal portions 24, 24' from the lateral portions 26, 26' and the central portion 28. The division 12 may be a crease formed by the casing 10 or a webbing separating the portions of the casing 10. In effect, the division 12 can consist of any arrangement that permits the casing 10 to be divided into portions which are connected to one another but can be flexed around a central portion 28 both before and after interengagement of the filler material 17.

The casing 10 includes a pad 14 positioned at the central portion 28 and is either secured onto or integrated into the casing 10. The pad 14 is configured and dimensioned to accommodate the distal end of a body member. The pad 14 can include hook and loop fasteners or other fastening elements (not shown) disposed on one side thereof that correspond to hook and loop fasteners or fastening elements (not shown) positioned on the central portion 28 of the casing 10 so that the pad 14 can be removed and replaced if necessary.

FIG. 3 is a perspective view of the casing 10 with straps 18 connected to longitudinal portion 24. The straps 18 include connection elements (not shown) disposed at the ends thereof such as hook and loop patches, buckles or snap elements which connect to opposing ends of respective straps 18.

While the illustrated shape of the casing 10 is not to be construed as limiting of the present invention, the gist of the present invention is a sealed casing containing a filler material 17 that is configured and dimensioned to easily enclose a body member. For example, the casing 10 may comprise of the shape of a circle or a rectangle that include foldable portions to enclose a body member.

Figure 5:
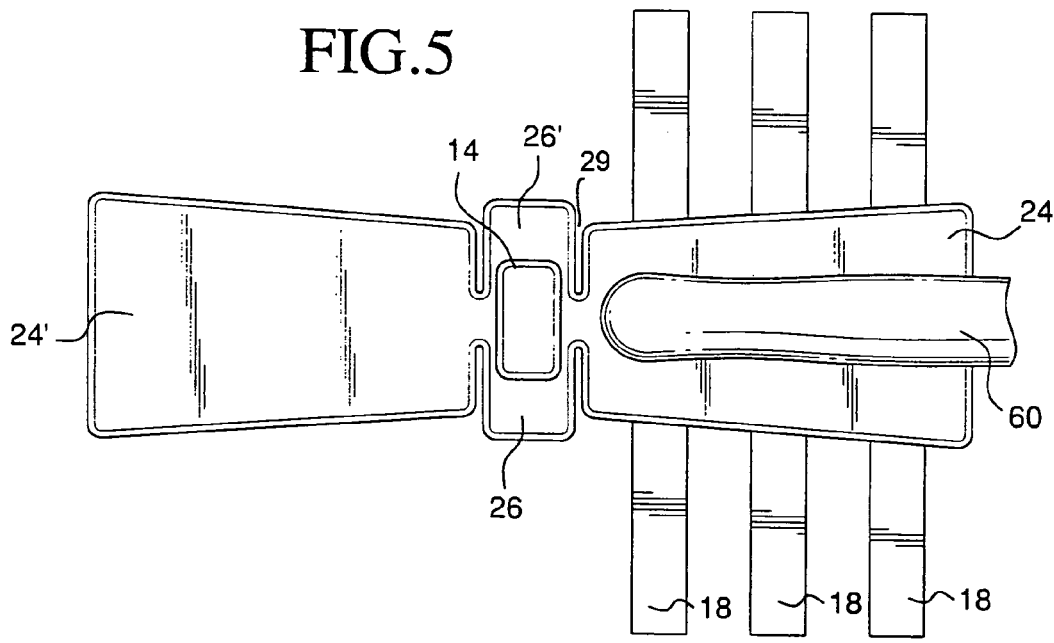
FIG. 5 is a perspective view showing a body member positioned along the wound dressing.
Figure 6:
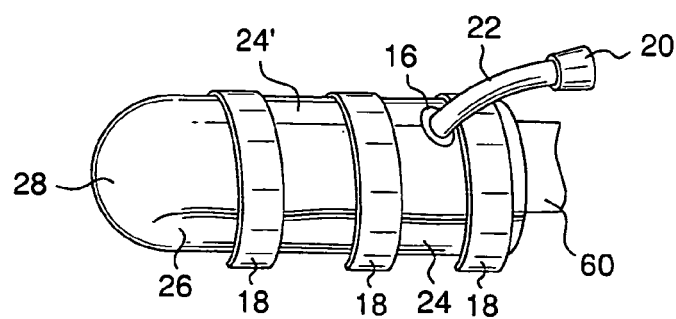
FIG. 6 is a perspective view showing the wound dressing connected to a vacuum device and folded over portions of the body member prior to evacuation of air from the interior of the sealed casing.

A method for applying the wound dressing to a body Member is exemplified in FIGS. 4–6. FIG. 4 shows a first step wherein the casing 10 is placed along a substantially flat surface in an extended configuration so that the filler material 17 is evenly distributed in the casing 10. FIG. 5 shows the next step wherein a body member 60 is positioned onto longitudinal portion 24. FIG. 6 shows the following step wherein the longitudinal portion 24' is folded to enclose the body member 60. Also shown is lateral portion 26 which is tucked under longitudinal portion 24' to also enclose the body member 60. Although not shown, it follows that lateral portion 26' is also tucked under the folded longitudinal portion 24'. The straps 18 are wrapped around longitudinal portions 24, 24' to thereby secure the casing 10 to the body member 60.

The next step is also shown in FIG. 6 which is to connect a vacuum device 20 to the valve 16 via a tube 22. Vacuum device 20 is used to perform the step of evacuating air from the interior of the casing 10.

Figure 7:
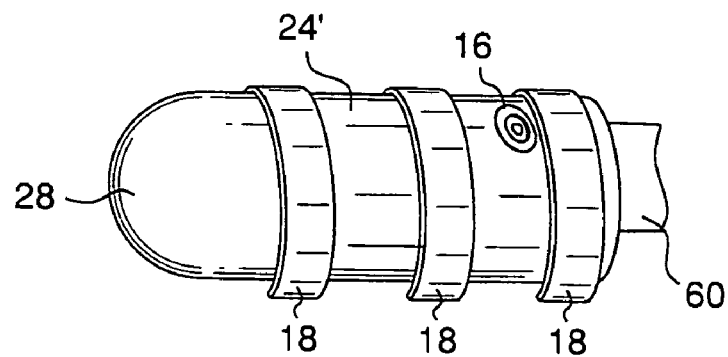
FIG. 7 is a perspective view showing the wound dressing after evacuation of air from the interior of the sealed casing.

FIG. 7 shows a rigid casing 10 after air has been evacuated from the interior of the casing 10 and the filler material 17 has interengaged. The casing 10 conforms to the shape of the body member 60.

Figure 8:
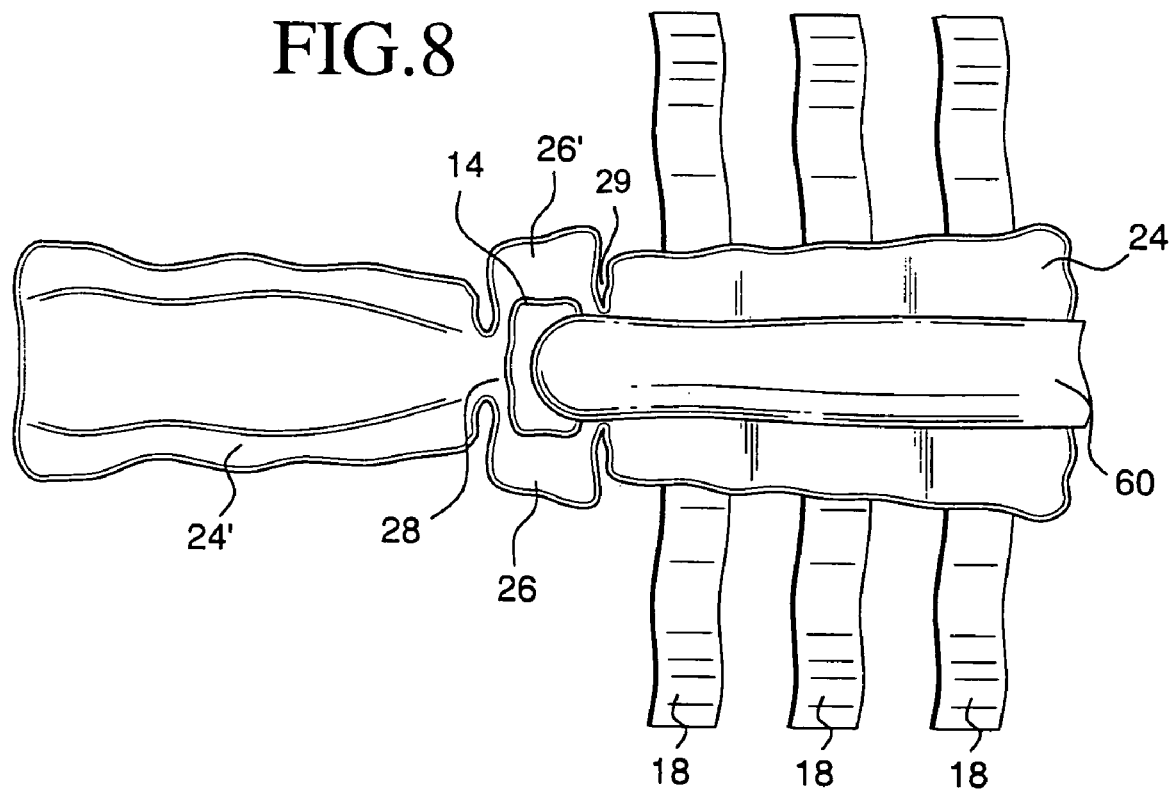
FIG. 8 is a perspective view showing the wound dressing opened for inspection of the body member.

FIG. 8 shows the rigid casing 10 opened for inspection of the body member 60 whereby the straps 18 are unsecured and longitudinal portion 24' and lateral portions 26, 26' are folded away from the body member 60.

The specific embodiments of the invention described herein are intended to be illustrative only and various modifications thereto may be envisioned and implemented by a person skilled in the art without departing from the spirit and scope of the invention which is defined in the claims that follow.

We claim:

1. A method for applying a wound dressing to a body member, the wound dressing including a sealed casing defining a central portion and a plurality of elongate flaps and lateral flaps having an interior with a compactable filler material disposed therein, the wound dressing further comprises a valve for introducing and evacuating air from the interior of the casing, the method comprising the steps of:
   placing the wound dressing along a substantially flat surface in an extended configuration wherein the elongate and lateral flaps, and the central portion extend along said flat surface to thereby evenly distribute the filler material disposed in the casing;
   positioning the body member onto a first one of the elongate flaps;
   folding the lateral flaps towards the body member and the central portion;
   folding a second one of the elongate flaps over the first elongate flap;
   connecting a vacuum device to the valve; and
   evacuating air from the interior of the casing while maintaining the body member in a predetermined position to cause the filler material to interengage to form a rigid structure conforming to the body member.

2. The method according to claim 1, further comprising the step of wrapping the at least one strap around the elongate flaps to secure the wound dressing to the body member.

3. A wound dressing for a body member, comprising:
   a sealed casing having an interior cavity and formed of a flexible, air impermeable material configured to accommodate and enclose a body member, the casing defining a central portion and a plurality of flaps including a first elongate flap having first and second ends and a first lateral flap extending from the central portion in a direction generally perpendicular to the first elongate flap, the first end of the first elongate flap connected to a first side of the central portion whereat a division is defined arranged to permit folding of the first elongate flap relative to the central portion; and
   a compactable filler material disposed in the interior of said casing.

4. The wound dressing according to claim 3, wherein the wound dressing comprises an extended configuration such that the central portion and the plurality of flaps define a plurality of substantially flat surfaces, and a wrapped configuration such that the portion and the plurality of flaps define a substantially non-flat configuration accommodating a body member.

5. The wound dressing according to claim 3, wherein the casing defines at least one recess located between the first side of the central portion and the first end of the first elongate flap.

6. The wound dressing according to claim 3, wherein the central portion and the first elongate flap are contiguously connected.

7. The wound dressing according to claim 3, wherein the first elongate flap defines a tapered width between the second and first ends thereof, the second end defining a greater width than the first end.

8. The wound dressing according to claim 3, further comprising a valve communicating with the interior of the casing for evacuating air therefrom, whereupon the filler material interengages, in the aggregate, to form a rigid structure in combination with the casing conforming to a body member.

* * * * *